United States Patent
Bradfisch et al.

(10) Patent No.: US 7,091,177 B2
(45) Date of Patent: *Aug. 15, 2006

(54) BACILLUS THURINGIENSIS ISOLATES ACTIVE AGAINST WEEVILS

(75) Inventors: Gregory A. Bradfisch, San Diego, CA (US); H. Ernest Schnepf, San Diego, CA (US); Leo Kim, Carlsbad, CA (US)

(73) Assignee: Mycogen Corporation, Indianapolis, IN (US)

( * ) Notice: Subject to any disclaimer, the term of this patent is extended or adjusted under 35 U.S.C. 154(b) by 424 days.

This patent is subject to a terminal disclaimer.

(21) Appl. No.: 10/631,405

(22) Filed: Jul. 30, 2003

(65) Prior Publication Data

US 2004/0033953 A1 Feb. 19, 2004

Related U.S. Application Data

(60) Division of application No. 09/737,228, filed on Dec. 14, 2000, now Pat. No. 6,605,462, which is a division of application No. 09/401,890, filed on Sep. 23, 1999, now Pat. No. 6,180,775, which is a continuation of application No. 09/005,280, filed on Jan. 9, 1998, now abandoned, which is a continuation of application No. 08/399,311, filed on Mar. 6, 1995, now Pat. No. 5,707,619.

(51) Int. Cl.
*A01N 37/18* (2006.01)
*C07K 14/325* (2006.01)

(52) U.S. Cl. .............................. 514/2; 530/350; 514/12
(58) Field of Classification Search ..................... None
See application file for complete search history.

(56) References Cited

U.S. PATENT DOCUMENTS

| | | | |
|---|---|---|---|
| 4,448,885 A | 5/1984 | Schnepf et al. | |
| 4,467,036 A | 8/1984 | Schnepf et al. | |
| 4,771,131 A | 9/1988 | Herrnstadt et al. | |
| 4,797,276 A | 1/1989 | Herrnstadt et al. | |
| 4,849,217 A | 7/1989 | Soares et al. | |
| 4,853,331 A | 8/1989 | Herrnstadt et al. | |
| 4,918,006 A | 4/1990 | Ellar et al. | |
| 4,935,236 A | 6/1990 | Herrnstadt et al. | |
| 4,948,734 A | 8/1990 | Edwards et al. | |
| 4,996,155 A | 2/1991 | Sick et al. | |
| 5,002,765 A | 3/1991 | Herrnstadt et al. | |
| 5,064,648 A | 11/1991 | Hickle et al. | |
| 5,104,974 A | 4/1992 | Sick et al. | |
| 5,133,962 A | 7/1992 | Sick et al. | |
| 5,262,324 A | 11/1993 | Payne | |
| 5,262,399 A | 11/1993 | Hickle et al. | |
| 5,273,746 A | 12/1993 | Payne et al. | |
| 5,277,905 A | 1/1994 | Foncerrada et al. | |
| 5,286,486 A | 2/1994 | Payne et al. | |
| 5,298,245 A | 3/1994 | Payne et al. | |
| 5,302,387 A | 4/1994 | Payne et al. | |
| 5,306,494 A | 4/1994 | Payne | |
| 5,359,048 A | 10/1994 | Ohba et al. | |
| 5,366,892 A | 11/1994 | Foncerrada et al. | |
| 5,378,625 A | 1/1995 | Donovan et al. | |
| 5,427,786 A | 6/1995 | Payne et al. | |
| 5,436,002 A | 7/1995 | Payne et al. | |
| 5,439,881 A | 8/1995 | Narva et al. | |
| 5,466,597 A | 11/1995 | Peferoen et al. | |
| 5,489,432 A | 2/1996 | Payne et al. | |
| 5,554,534 A | 9/1996 | Michaels et al. | |
| 5,707,619 A | 1/1998 | Bradfisch et al. | |
| 5,723,440 A * | 3/1998 | Stockhoff et al. | ............. 514/12 |
| 5,747,450 A | 5/1998 | Ohba et al. | |
| 5,824,878 A | 10/1998 | Ohba et al. | |
| 6,180,775 B1 * | 1/2001 | Bradfisch et al. | ......... 536/23.71 |

FOREIGN PATENT DOCUMENTS

| | | |
|---|---|---|
| EP | 0 238 311 | 9/1987 |
| EP | 0 324 254 | 7/1989 |
| EP | 0 382 990 | 8/1990 |
| EP | 0 498 537 | 8/1992 |
| EP | 0 500 311 | 8/1992 |
| EP | 0 711 834 | 10/1994 |
| WO | WO 91/16433 | 10/1991 |
| WO | WO 93/03154 | 2/1993 |
| WO | WO 93/15206 | 5/1993 |
| WO | WO 93/14641 | 8/1993 |
| WO | WO 95/02693 | 1/1995 |

OTHER PUBLICATIONS

Adams et al., "Elucidation of the mechanism of CryIIA overproduction in a mutagenized strain of *Bacillus thuringiensis* var. *Tenebrionis*," Mol. Micro. (1994), pp. 381-389, vol. 14.

Beegle, C.C., "Use of Entomogenous Bacteria in Agroecosystems," Developments in Industrial Microbiology (1978), pp. 97-104, vol. 20.

Carbonell, R.M., "Pathogens and Nematodes for Control of Rice Water Weevil in Cuba," Informational Rice Research Newsletter (1983), pp. 16-17, vol. 8, iss. 6.

Couch, T.L., "Mosquito Pathogenicity of *Bacillus thuringiensis* var. *israelensis*," Developments in Industrial Microbiology (1980), pp. 61-76, vol. 22.

Donovan et al., "Isolation and characterization of EG2158, a new strain of *Bacillus thuringiensis* toxic to coleopteran . . . ," Mol. Gen. Genet. (1988), pp. 365-372, vol. 214.

(Continued)

*Primary Examiner*—Gabriele Bugaisky
(74) *Attorney, Agent, or Firm*—Saliwanchik, Lloyd & Saliwanchik

(57) ABSTRACT

The subject invention concerns the discovery of *Bacillus thuringiensis* isolates with advantageous activity against weevils. In preferred embodiments of the invention, B.t. isolates, or toxins therefrom, are used to control alfalfa weevils, boll weevils, and/or rice water weevils. The toxins can be administered to the pests through a variety of methods including the transformation of bacteria or plants to produce the weevil-active toxins.

8 Claims, No Drawings

OTHER PUBLICATIONS

Donovan et al., "Characterization of two genes encoding *Bacillus thuringiensis* insecticidal crystal . . . ," Applied & Environ. Microbiol. (1992), pp. 3921-3927, vol. 58.

Feitelson et al., "*Bacillus thuringiensis*: Insects and Beyond," Bio/Technology (1992), pp. 271-275, vol. 10.

Gaertner et al., "Current Applied Recombinant DNA Projects," TIBTECH (1988), pp. S4-S7, vol. 6.

Gaertner, F.H., "Cellular delivery systems for insecticidal proteins . . . ," Controlled Delivery of Crop-Protection Agents (1989), pp. 245-255.

Herrnstadt et al., "Nucleotide sequence and deduced amino acid sequence of a coleopteran-active delta-endotoxin gene from Bacillus . . . ," Gene (1987), pp. 37-46, vol. 57.

Hofte et al., "Nucleotide sequence of a gene encoding an insecticidal protien of *Bacillus thuringiensis* var. *tenebrionis* toxic . . . ," Nucleic Acids Res. (1987), p. 7183, vol. 15.

Hofte et al., "Insecticidal Crystal Proteins of *Bacillus thuringiensis*," Microbiological Reviews (1989), pp. 242-255, vol. 52, iss. 2.

Jaquet et al., "Specificity of *Bacillus thuringiensis* Delta-Endotoxin," Applied and Environmental Microbiology (1987), pp. 500-504, vol. 53, iss. 3.

Krieg et al., "*Bacillus thuringiensis* var. *tenebrionis*: ein neuer, gegenuber Larven von Coleopteran Wirksamer Pathotyp," Z. ang. Ent. (1983), pp. 500-508, vol. 96.

Lambert et al., "Novel *Bacillus thuringiensis* Insecticidal Crystal Protein with a Silent Activity . . . ," Appl. and Environ. Microbiol. (1992), pp. 2536-2542, vol. 58, iss. 8.

Lambert et al., "Nucleotide sequence of gene crylllD encoding a novel coleopteran-active crystal protein from strain . . . ," Gene (1992), pp. 131-132, vol. 110.

McPherson et al., "Characterization of the coleopteran-specific protein gene of *Bacillus thuringiensis* var. *tenebrionis*," Bio/technology (1988), pp. 61-66, vol. 6.

Nagata, T., "Rice Production and Insect Control in Asia," Agrochem. Jpn. (1993), pp. 21-23, vol. 63 (ABSTRACT).

Prefontaine et al., "Use of Oligonucleotide Probes to Study the Relatedness of Delta-Endotoxin . . . ," Appl. and Environ. Microbiol. (1987), pp. 2808-2814, vol. 53, iss. 12.

Schnepf et al., "Cloning and expression of the *Bacillus thuringiensis* crystal protein gene in *Escherichia coli*," Proc. Natl. Acad. Sci. USA (1981), pp. 2893-2897, vol. 78, iss. 5.

Sekar et al., "Molecular cloning and characterization of the insecticidal crystal protein gene of *Bacillus thuringiensis*. . . ," Proc. Natl. Acad. Sci. (1987), pp. 7036-7040, vol. 84.

Sick et al., "Nucleotide sequence of a coleopteran-active toxin gene from a new isolate of *Bacillus thuringiensis* subsp. tolworthi," Nucleic Acids Res. (1990), p. 1305, vol. 18.

Smith, M.C., "The Rice Water Weevil, *Lissorhoptrus oryzophilus* Kuschel," Exotic Plant Quarantine Pests and Possibilities for Introduction of Plant Material (1983), pp. 3-9.

Teixeira De Souza et al., "Full expression of the crylllA toxin gene of *Bacillus thuringiensis* requries a distant upstream . . . ," J. Bact. (1993), pp. 2952-2960, vol. 175.

* cited by examiner

BACILLUS THURINGIENSIS ISOLATES ACTIVE AGAINST WEEVILS

CROSS-REFERENCE TO A RELATED APPLICATION

This is a divisional of Ser. No. 09/737,228, filed Dec. 14, 2000 now U.S. Pat. No. 6,605,462, which was a divisional of Ser. No. 09/401,890, filed Sep. 23, 1999, now U.S. Pat. No. 6,180,775, which was a continuation of Ser. No. 09/005,280, filed Jan. 9, 1998, now abandoned, which was a continuation of Ser. No. 08/399,311, filed Mar. 6, 1995, now U.S. Pat. No. 5,707,619.

FIELD OF THE INVENTION

The present invention relates to methods of controlling weevils. In particular, δ-endotoxins of *Bacillus thuringiensis* (*B.t.*) have been discovered to control rice water weevils, alfalfa weevils, and boll weevils.

BACKGROUND OF THE INVENTION

The soil microbe *Bacillus thuringiensis* (*B.t.*) is a Gram-positive, spore-forming bacterium characterized by parasporal crystalline protein inclusions. These inclusions often appear microscopically as distinctively shaped crystals. The proteins can be highly toxic to pests and specific in their toxic activity. Certain *B.t.* toxin genes have been isolated and sequenced, and recombinant DNA-based *B.t.* products have been produced and approved for use. In addition, with the use of genetic engineering techniques, new approaches for delivering *B.t.* endotoxins to agricultural environments are under development, including the use of plants genetically engineered with endotoxin genes for insect resistance and the use of stabilized intact microbial cells as *B.t.* endotoxin delivery vehicles (Gaertner and Kim, 1988). Thus, isolated *B.t.* endotoxin genes are becoming commercially valuable.

Until the last fifteen years, commercial use of *B.t.* pesticides has been largely restricted to a narrow range of lepidopteran (caterpillar) pests. Preparations of the spores and crystals of *B. thuringiensis* var. *kurstaki* have been used for many years as commercial insecticides for lepidopteran pests. For example, *B. thuringiensis* var. *kurstaki* HD-1 produces a crystal called a δ-endotoxin which is toxic to the larvae of a number of lepidopteran insects.

In recent years, however, investigators have discovered *B.t.* pesticides with specificities for a much broader range of pests. For example, other species of *B.t.*, namely *B.t.* var. *israelensis* and *B.t.* var. *tenebrionis* (a.k.a. M-7, a.k.a. *B.t.* var. *san diego*), have been used commercially to control insects of the orders Diptera and Coleoptera, respectively (Gaertner, 1989). See also Couch, 1980 and Beegle, 1978. Krieg et al., 1983, describe *Bacillus thuringiensis* var. *tenebrionis*, which is reportedly active against two beetles in the order Coleoptera. These are the Colorado potato beetle, *Leptinotarsa decemlineata*, and the beetle *Agelastica alni*.

Recently, new subspecies of *B.t.* have been identified, and genes responsible for active δ-endotoxin proteins have been isolated (Höfte and Whiteley, 1989). Höfte and Whiteley classified *B.t.* crystal protein genes into 4 major classes. The classes were CryI (Lepidoptera-specific), CryII (Lepidoptera- and Diptera-specific), CryIII (Coleoptera-specific), and CryIV (Diptera-specific). Prefontaine et al., 1987, describe probes useful in classifying lepidopteran-active genes. The discovery of strains specifically toxic to other pests has been reported (Feitelson et al., 1992).

*B.t.* crystalline toxins are generally recognized as being protoxins, requiring either particular physicochemical conditions (i.e., pH, redox, ionic strength), or the action of certain proteases, or both, to generate an active toxin (Höfte and Whiteley, 1989). In most cases, the insect supplies conditions for activation of the toxin; however, cases have been documented where pre-solubilization or pre-proteolysis have been necessary for optimum activity (Jacquet et al., 1987) or detection of activity (Höfte et al., 1992).

The cloning and expression of a *B.t.* crystal protein gene in *Escherichia coli* has been described in-the published literature (Schnepf and Whiteley, 1981). U.S. Pat. Nos. 4,448,885 and 4,467,036 both disclose the expression of *B.t.* crystal proteins in *E. coli*. U.S. Pat. Nos. 4,797,276 and 4,853,331 disclose *B. thuringiensis* var. *tenebrionis* (a.k.a. *B.t. san diego*, a.k.a. M-7) which can be used to control coleopteran pests in various environments. U.S. Pat. No. 4,918,006 discloses *Bacillus thuringiensis* var. *israelensis* toxins which are active against dipteran pests and reports that a protein of about 27 kD, and fragments thereof, are responsible for the dipteran activity. U.S. Pat. No. 4,849,217 discloses *B.t.* isolates which have activity against the alfalfa weevil. U.S. Pat. No. 5,151,363 and U.S. Pat. No. 4,948,734 disclose certain isolates of *B.t.* which have activity against nematodes. As a result of extensive research and investment of resources, other patents have issued for new *B.t.* isolates and new uses of *B.t.* isolates. However, the discovery of new *B.t.* isolates and new uses of known *B.t.* isolates remains an empirical, unpredictable art.

The alfalfa weevil, *Hypera postica*, and the closely related Egyptian alfalfa weevil, *Hypera brunneipennis*, are the most important insect pests of alfalfa grown in the United States, with 2.9 million acres infested in 1984. An annual sum of 20 million dollars is spent to control these pests. The Egyptian alfalfa weevil is the predominant species in the southwestern U.S., where it undergoes aestivation (i.e., hibernation) during the hot summer months. In all other respects, it is identical to the alfalfa weevil, which predominates throughout the rest of the U.S.

The larval stage is the most damaging in the weevil life cycle. By feeding at the alfalfa plant's growing tips, the larvae cause skeletonization of leaves, stunting, reduced plant growth, and, ultimately, reductions in yield. Severe infestations can ruin an entire cutting of hay. The adults, also foliar feeders, cause additional, but less significant, damage.

The rice water weevil, *Lissorhoptrus aryzophilus*, is a major insect pest of rice in North America and Southeast Asia. See Smith, M. C. (1983) "The Rice Water Weevil, *Lissorhoptrus oryzophilus* Kuschel," *Exotic Plant Quarantine Pests and Possibilities for Introduction of Plant Materials*, pp. 3–9. The rice water weevil can be directly responsible for average yield reductions of 10% or more if not treated with the proper insecticides. Rice water weevil larvae cause significant damage to the root systems of cultivated rice. Adult rice water weevils are small, black, oblong weevils (2.8–3.2 mm long×1.2–1.8 mm wide) with gray scales. Adults feed on rice by rasping away the leaf epidermis leaving skeletonized longitudinal slits on the upper leaf blades. Adult weevils appear to prefer two-week old rice plants over those of seven-week old plants and increased levels of nitrogen fertilizers increase the level of feeding. Adults also feed on individual grains of headed rice consuming the floral part or the endosperm of the developing rice kernel. Weevils enter a true diapause, fly to hibernation sites as early as July and overwinter in bunch grasses, Spanish moss and ground trash. Upon emerging in the spring the weevils migrate to flooded rice fields where they mate.

Eggs are deposited in submerged leaf sheaths on the lower part of the rice plant and hatch within 4–9 days.

The rice water weevil larvae have 4 instars. The length of each instar phase is temperature dependent and under normal field conditions the larval stages last about 27 days. The larvae have paired dorsal tracheal hooks which function as modified spiracles. The apical segment of the hook is heavily sclerotized and is used to pierce root tissue and sequester air. This allows the larvae to live below the water surface. The pupae form in an oval, water-tight mud cell and resembles the adult in size and shape but is white in color. The duration of the pupal stage is seven days at 27° C. Two and three generations per season have been reported.

Control of the rice water weevil is difficult due to its terrestrial, aquatic and soil habitats. Chemical insecticides have been used in the past with limited success. Native resistant rice cultivars are being sought with only low to moderate resistant lines being discovered.

The *International Rice Research Newsletter* (1983) Vol. 8, No. 6, pp. 16–17, reports pathogens and nematodes for the control of rice water weevil. Various strains of fungi (*Beauveria bassiana* and *Metarrhizium anisopliae*) and nematodes were shown to control rice water weevils. None of the *B.t.* biopreparations controlled rice water weevils when applied to 35 day old rice plants as a foliar spray at 0.6, 1.2 and 2.4 kg/ha.

It has been unexpectedly discovered that *B.t.* δ-endotoxins are effective in controlling rice water weevils contrary to published reports that *B.t.* biopreparations were ineffective in controlling this pest.

BRIEF SUMMARY OF THE INVENTION

The subject invention concerns the use of *Bacillus thuringiensis* (*B.t.*) isolates and δ-endotoxins therefrom to control weevil pests. Specifically exemplified herein is the use of *B.t.* isolates and toxins to control alfalfa weevils, boll weevils, and rice water weevils.

In one preferred embodiment of the present invention, *B.t.* δ-endotoxins are employed to control rice water weevils. The *B.t.* δ-endotoxin is administered to rice water weevils in a manner wherein the rice water weevils ingest the toxin. The *B.t.* δ-endotoxins may be applied as a foliar spray to rice crops where adult weevils graze. Also, a *B.t.* structural gene may be inserted into the rice plant genome to produce the δ-endotoxin in planta throughout the plant or in specific plant tissues to control both adults and larvae.

In one preferred embodiment of the subject invention, *B.t.* toxins of the CryIII class are used to control weevil pests. For example, a CryIII *B.t.* isolate HD511 has shown excellent activity against the rice water weevil.

Further exemplified herein is the use of *B.t.* isolates PS50C, PS201T6, KB92, PS86B1, PS101Z2, PS50B, PS204G4, PS204G6, PS167P, PS192N1, PS201L1, PS169E, PS177G, PS196S1, and PS73E to control weevils.

In another embodiment of the subject invention, the materials and methods set forth herein pertain particularly to *Bacillus thuringiensis* var. *israelensis*, or toxins therefrom, to control weevils. A related embodiment concerns the use of an activated toxin from *B.t.* isolate PS201T6 to control weevils.

As described herein, the toxins from the *B.t.* strains HD511, PS73E, PS192N1 and PS201T6 (activated toxin) are particularly effective in controlling rice water weevils. The PS201T6 activated toxin is also highly active against cotton boll weevil.

The subject invention also includes the use of variants of the exemplified *B.t.* isolates which have substantially the same pesticidal properties as the exemplified isolate. These variants include mutants. Procedures for making mutants are well known in the microbiological art. Ultraviolet light and chemical mutagens such as nitrosoguanidine are used extensively toward this end.

Recombinant hosts which have been transformed to express *B.t.* toxins can also be used according to the subject invention. These recombinant hosts maybe, for example, microorganisms or plants. Specifically exemplified herein is the recombinant microorganism designated MR506.

According to the subject invention, weevils may be controlled using the isolates themselves, variants of the isolates, δ-endotoxins obtained from said isolates, commercial preparations made from cultures of these isolates, or toxins produced by DNA of these isolates. In one embodiment, the toxins may be produced by DNA which has been transformed into another host. Further, the invention also includes the treatment of substantially intact cells of either a *B.t.* isolate or recombinant cells containing DNA from a *B.t.* isolate, to prolong the pesticidal activity when the substantially intact cells are applied to the environment of a target pest.

DETAILED DISCLOSURE OF THE INVENTION

The subject invention concerns the discovery of a new method for controlling weevils which involves contacting the weevils with a *Bacillus thuringiensis* (*B.t.*) isolate or a δ-endotoxin therefrom. Several *B.t.* isolates with excellent activity against weevils are described herein.

In one specific embodiment of the present invention, one or more *B.t.* δ-endotoxins are administered to rice water weevils to control this pest in rice crops. The *B.t.* δ-endotoxin is administered in a manner wherein the weevils ingest the toxin to allow the toxin to disrupt the epithelial cell wall of the midgut. As would be appreciated by one skilled in the art, the exact method of administration is not critical. For example, the *B.t.* δ-endotoxins can be administered as a foliar spray onto rice crops. This method of administration is effective in controlling adult weevils that feed on the leaves of rice plants. Another method of administration is accomplished by inserting a *B.t.* insecticidal structural gene into a rice plant genome whereby the δ-endotoxin is produced in vivo in the plant. Both adults and larvae grazing on the transgenic plant will ingest the δ-endotoxin. Advantageously, tissue-specific promoters can be employed to drive the expression of the *B.t.* gene so that the toxin is present in the tissue which is most likely to be eaten by the weevil. For example, root specific promoters can be employed to provide control of larvae and leaf specific promoters can be employed to control adult weevils.

In one embodiment of the subject invention, the *B.t.* isolates utilized are *B.t.* var. *israelensis*, or toxins therefrom. The *israelensis* variety is well known and readily recognized by those skilled in this art. Characteristics generally associated with the *israelensis* category of *B.t.* include dipteran activity, H14 serotype, and a protein pattern which includes an approximately 28 to 33 kD protein and, generally, additional proteins of about 70 kD and 130 kD. Other *B.t.* varieties which express *israelensis*-type toxins can also be used according to the subject invention. Such toxins would have a size similar to the toxins produced by *B.t.i.* and a similar activity profile. *B.t.* isolates of the var. *morrisoni* serotype 8a,8b have, for example, been reported to express *B.t.i.*-typetoxins. An example of such an isolate is PS71M3.

As used herein, the term "*Bacillus thuringiensis* var. *israelensis* toxin" includes toxins which are similar or related to toxins expressed by *B.t.i.* but which happen to be expressed by a different variety of *B.t.*

In one preferred embodiment of the subject invention, an activated toxin from *B.t.* isolate PS201T6 is used to achieve excellent control of weevils. Similarly, toxins from *B.t.i.* may also be activated by, for example, growing a *Bacillus thuringiensis* var. *israelensis* under conditions which facilitate the activation of said toxin by the action of compounds which exist naturally or are produced in said culture. Activation may also be achieved by adding a compound to a *Bacillus thuringiensis* var. *israelensis* culture, or a supernatant thereof, wherein said compound participates in the activation of said toxin either through direct action on said toxin or by facilitating the action of a second compound. The additional compound may be, for example, a protease, or a compound which raises the pH of the culture or supernatant.

The cultures disclosed in this application have been deposited in the Agricultural Research Service Patent Culture Collection (NRRL), Northern Regional Research Center, 1815 North University Street, Peoria, Ill. 61604, USA.

TABLE 1

Culture deposit information

| Isolate | Deposit No. | Deposit Date |
|---|---|---|
| B. t. japonensis bui bui (KB92) | FERM BP-3465 | Jun. 26, 1992 |
| HD511 | Howard Dulmage Collection, Texas | |
| PS33F2 | NRRL B-18244 | Jul. 28, 1987 |
| PS50B | NRRL B-21656 | Feb. 19, 1997 |
| PS50C | NRRL B-18746 | Jan. 9, 1991 |
| PS73E | NRRL B-21417 | Mar. 8, 1995 |
| PS86B1 | NRRL B-18299 | Feb. 2, 1988 |
| PS101Z2 | NRRL B-18890 | Oct. 1, 1991 |
| PS167P | NRRL B-18681 | Jul. 17, 1990 |
| PS169E | NRRL B-18682 | Jul. 17, 1990 |
| PS177G | NRRL B-18684 | Jul. 17, 1990 |
| PS192N1 | NRRL B-18721 | Oct. 5, 1990 |
| PS196S1 | NRRL B-18748 | Jan. 9, 1991 |
| PS201L1 | NRRL B-18749 | Jan. 9, 1991 |
| PS201T6 | NRRL B-18750 | Jan. 9, 1991 |
| PS204G4 | NRRL B-18685 | Jul. 17, 1990 |
| PS204G6 | NRRL B-18686 | Jul. 17, 1990 |

The subject cultures have been deposited under conditions that assure that access to the cultures will be available during the pendency of this patent application to one determined by the Commissioner of Patents and Trademarks to be entitled thereto under 37 CFR 1.14 and 35 U.S.C. 122. The deposits are available as required by foreign patent laws in countries wherein counterparts of the subject application, or its progeny, are filed. However, it should be understood that the availability of the deposits does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of a deposit, and in any case, for a period of at least thirty (30) years after the date of deposit or for the enforceable life of any patent which may issue disclosing the cultures. The depositor acknowledges the duty to replace the deposit(s) should the depository be unable to furnish a sample when requested, due to the condition of the deposit(s). All restrictions on the availability to the public of the subject culture deposits will be irrevocably removed upon the granting of a patent disclosing them.

Certain *B.t.* isolates, genes, and toxins useful according to the subject invention have been previously described in issued U.S. patents or published international patent documents. These isolates and their previously-discovered uses are tabulated below:

TABLE 2

| Isolate | Patent or Publication | Activity |
|---|---|---|
| KB92 (bui bui) | 5,359,048 | coleopterans |
| MR506 | WO93/04587 | lepidopterans |
| HD511 | 5,262,324 | coleopterans |
| | 5,286,486 | coleopterans |
| PS50C | 5,185,148 | scarabs |
| | 5,262,158 | mites |
| | 5,277,905 | coleopterans |
| | 5,286,485 | lepidopterans |
| PS86B1 | 4,966,765 | coleopterans |
| | 5,100,665 | lesser mealworms |
| | 5,185,148 | scarabs |
| PS167P | 5,151,363 | nematodes |
| PS169E | 5,151,363 | nematodes |
| PS177G | 5,151,363 | nematodes |
| PS192N1 | 5,262,160 | dipterans |
| | 5,273,746 | lice |
| PS196S1 | 5,298,245 | dipterans |
| PS201L1 | 5,298,245 | dipterans |
| PS201T6 | 5,273,746 | lice |
| | 5,298,245 | dipterans |
| | 5,302,387 | cockroaches |
| PS204G4 | 5,151,363 | nematodes |
| PS204G6 | 5,151,363 | nematodes |
| | 5,273,746 | lice |
| PS33F2 | 5,151,363 | nematodes |
| | 4,849,217 | coleopterans |

Nothing in those documents describes or suggests the unique activity described herein. The disclosures of those patents are incorporated herein by reference. Those patents contain, for example, descriptions of toxins and genes from the indicated isolates. Those toxins and genes can be used by one skilled in the art in conjunction with the teachings provided herein to control weevil pests.

Genes and toxins. In one embodiment of the subject invention, genes which encode *B.t.* toxins active against weevil pests are used to transform a suitable host. The genes and toxins useful according to the subject invention include not only the full length sequences but also fragments of these sequences, variants, mutants, and fusion proteins which retain the characteristic pesticidal activity of the toxins specifically exemplified. As used herein, the terms "variants" or "variations" of genes refer to nucleotide sequences which encode the same toxins or which encode equivalent toxins having pesticidal activity. As used herein, the term "equivalent toxins" refers to toxins having the same or essentially the same biological activity against the target pests as the claimed toxins.

It should be apparent to a person skilled in this art that genes encoding weevil-active toxins can be identified and obtained through several means. The genes may be obtained from the isolates deposited at a culture depository as described above. These genes, or portions or variants thereof, may also be constructed synthetically, for example, by use of a gene synthesizer. Variations of genes may be readily constructed using standard techniques for making point mutations. Also, fragments of these genes can be made using commercially available exonucleases or endonucleases according to standard procedures. For example, enzymes such as Bal31 or site-directed mutagenesis can be used to systematically cut off nucleotides from the ends of these genes. Also, genes which encode active fragments may be obtained using a variety of restriction enzymes. Proteases may be used to directly obtain active fragments of these toxins.

Equivalent toxins and/or genes encoding these equivalent toxins can be derived from *B.t.* isolates and/or DNA libraries using the teachings provided herein. There are a number of methods for obtaining the pesticidal toxins of the instant invention. For example, antibodies to the pesticidal toxins disclosed and claimed herein can be used to identify and isolate other toxins from a mixture of proteins. Specifically, antibodies may be raised to the portions of the toxins which are most constant and most distinct from other *B.t.* toxins. These antibodies can then be used to specifically identify equivalent toxins with the characteristic activity by immunoprecipitation, enzyme linked immunosorbent assay (ELISA), or Western blotting. Antibodies to the toxins disclosed herein, or to equivalent toxins, or fragments of these toxins, can readily be prepared using standard procedures in this art. The genes which encode these toxins can then be obtained from the microorganism.

Fragments and equivalents which retain the pesticidal activity of the exemplified toxins would be within the scope of the subject invention. Also, because of the redundancy of the genetic code, a variety of different DNA sequences can encode the amino acid sequences disclosed herein. It is well within the skill of a person trained in the art to create these alternative DNA sequences encoding the same, or essentially the same, toxins. These variant DNA sequences are within the scope of the subject invention. As used herein, reference to "essentially the same" sequence refers to sequences which have amino acid substitutions, deletions, additions, or insertions which do not materially affect pesticidal activity.

A further method for identifying the toxins and genes of the subject invention is through the use of oligonucleotide probes. These probes are nucleotide sequences having a means for detection. As is well known in the art, if the probe molecule and nucleic acid sample hybridize by forming a strong bond between the two molecules, it can be reasonably assumed that the probe and sample have substantial homology. The probe's means of detection provides a means for determining in a known manner whether hybridization has occurred. Such a probe analysis provides a rapid method for identifying toxin-encoding genes of the subject invention. The nucleotide segments which are used as probes according to the invention can be synthesized by use of DNA synthesizers using standard procedures. These nucleotide sequences can also be used as PCR primers to amplify genes of the subject invention.

Recombinant hosts. The toxin-encoding genes harbored by the isolates disclosed herein can be introduced into a wide variety of microbial or plant hosts. Expression of the toxin gene results, directly or indirectly, in the production of the toxin. With suitable microbial hosts, e.g., *Pseudomonas,* the microbes can be applied to the situs of the pest, where they will proliferate and be ingested by the pest, resulting in control of the pest. Alternatively, the microbe hosting the toxin gene can be treated under conditions that prolong the activity of the toxin and stabilize the cell. The treated cell, which retains the toxic activity, then can be applied to the environment of the target pest.

Where the *B.t.* toxin gene is introduced via a suitable vector into a microbial host, and said host is applied to the environment in a living state, it is advantageous to use certain host microbes. For example, microorganism hosts can be selected which are known to occupy the pest's habitat. Microorganism hosts may also live symbiotically with a specific species of weevil. These microorganisms are selected so as to be capable of successfully competing in the particular environment with the wild-type microorganisms, provide for stable maintenance and expression of the gene expressing the polypeptide pesticide, and, desirably, provide for improved protection of the pesticide from environmental degradation and inactivation.

A wide variety of ways are available for introducing a *B.t.* gene encoding a toxin into a microorganism host under conditions which allow for stable maintenance and expression of the gene. These methods are well known to those skilled in the art and are described, for example, in U.S. Pat. No. 5,135,867, which is incorporated herein by reference.

Furthermore, materials and methods for introducing *B.t.* genes into plants in order to confer upon such plants the ability to produce insecticidal toxins is well known in the art. In a preferred embodiment, the *B.t.* genes are modified to facilitate optimal stability and expression in the selected plant host. In this regard, U.S. Pat. No. 5,380,831 is incorporated herein by reference.

Treatment of cells. As mentioned above, *B.t.* or recombinant cells expressing a *B.t.* toxin can be treated to prolong the toxin activity and stabilize the cell by forming a cellular microcapsule. The pesticide microcapsule that is formed comprises the *B.t.* toxin within a cellular structure that has been stabilized and will protect the toxin when the microcapsule is applied to the environment of the target pest. Suitable host cells may include either prokaryotes or eukaryotes, normally being limited to those cells which do not produce substances toxic to higher organisms, such as mammals. However, organisms which produce substances toxic to higher organisms could be used, where the toxic substances are unstable or the level of application sufficiently low as to avoid any possibility of toxicity to a mammalian host. As hosts, of particular interest will be the prokaryotes and the lower eukaryotes, such as fungi.

The cell will usually be intact and be substantially in the proliferative form when treated, rather than in a spore form, although in some instances spores may be employed.

Treatment of the microbial cell, e.g., a microbe containing the *B.t.* toxin gene, can be by chemical or physical means, or by a combination of chemical and/or physical means, so long as the technique does not deleteriously affect the properties of the toxin, nor diminish the cellular capability of protecting the toxin. Examples of chemical reagents are halogenating agents, particularly halogens of atomic no. 17–80. More particularly, iodine can be used under mild conditions and for sufficient time to achieve the desired results. Other suitable techniques include treatment with aldehydes, such as glutaraldehyde; anti-infectives, such as zephiran chloride and cetylpyridinium chloride; alcohols, such as isopropyl and ethanol; various histologic fixatives, such as Lugol iodine, Bouin's fixative, various acids, and Helly's fixative (See: Humason, 1967); or a combination of physical (heat) and chemical agents that preserve and prolong the activity of the toxin produced in the cell when the cell is administered to the host animal. Examples of physical means are short wavelength radiation such as gamma-radiation and X-radiation, freezing, UV irradiation, lyophilization, and the like. Methods for treatment of microbial cells are disclosed in U.S. Pat. Nos. 4,695,455 and 4,695,462, which are incorporated herein by reference.

Growth of cells. The cellular host containing the B.t. insecticidal gene may be grown in any convenient nutrient medium, where the DNA construct provides a selective advantage, providing for a selective medium so that substantially all or all of the cells retain the B.t. gene. These cells may then be harvested in accordance with conventional ways. Alternatively, the cells can be treated prior to harvesting.

The B.t. cells of the invention can be cultured using standard art media and fermentation techniques. Upon completion of the fermentation cycle the bacteria can be harvested by first separating the B.t. spores and crystals from the fermentation broth by means well known in the art. The recovered B.t. spores and crystals can be formulated into a wettable powder, liquid concentrate, granules or other formulations by the addition of surfactants, dispersants, inert carriers, and other components to facilitate handling and application for particular target pests. These formulations and application procedures are all well known in the art.

Formulations. Formulated bait granules containing an attractant and spores and crystals of the B.t. isolates, or recombinant microbes comprising the genes obtainable from the B.t. isolates disclosed herein, can be applied to the environment of the weevil. The bait may be applied liberally since the toxin does not affect animals or humans. Product may also be formulated as a spray or powder. The B.t. isolate or recombinant host expressing the B.t. gene may also be incorporated into a bait or food source for the weevil.

As would be appreciated by a person skilled in the art, the pesticidal concentration will vary widely depending upon the nature of the particular formulation, particularly whether it is a concentrate or to be used directly. The pesticide will be present in at least 1% by weight and may be 100% by weight. The dry formulations will have from about 1–95% by weight of the pesticide while the liquid formulations will generally be from about 1–60% by weight of the solids in the liquid phase. Formulations that contain cells will generally have from about $10^2$ to about $10^4$ cells/mg. These formulations will be administered at about 50 mg (liquid or dry) to 1 kg or more per hectare.

The formulations can be applied to the environment of the weevils, e.g. on plant foliage.

Mutants. Mutants of the isolates described herein can be made by procedures well known in the art. For example, an asporogenous mutant can be obtained through ethylmethane sulfonate (EMS) mutagenesis of a novel isolate. The mutants can be made using ultraviolet light and nitrosoguanidine by procedures well known in the art.

A smaller percentage of the asporogenous mutants will remain intact and not lyse for extended fermentation periods; these strains are designated lysis minus (−). Lysis minus strains can be identified by screening asporogenous mutants in shake flask media and selecting those mutants that are still intact and contain toxin crystals at the end of the fermentation. Lysis minus strains are suitable for a cell treatment process that will yield a protected, encapsulated toxin protein.

To prepare a phage resistant variant of said asporogenous mutant, an aliquot of the phage lysate is spread onto nutrient agar and allowed to dry. An aliquot of the phage sensitive bacterial strain is then plated directly over the dried lysate and allowed to dry. The plates are incubated at 30° C. The plates are incubated for 2 days and, at that time, numerous colonies could be seen growing on the agar. Some of these colonies are picked and subcultured onto nutrient agar plates. These apparent resistant cultures are tested for resistance by cross streaking with the phage lysate. A line of the phage lysate is streaked on the plate and allowed to dry. The presumptive resistant cultures are then streaked across the phage line. Resistant bacterial cultures show no lysis anywhere in the streak across the phage line after overnight incubation at 30° C. The resistance to phage is then reconfirmed by plating a lawn of the resistant culture onto a nutrient agar plate. The sensitive strain is also plated in the same manner to serve as the positive control. After drying, a drop of the phage lysate is plated in the center of the plate and allowed to dry. Resistant cultures showed no lysis in the area where the phage lysate has been placed after incubation at 30° C. for 24 hours.

Following are examples which illustrate procedures, including the best mode, for practicing the invention. These examples should not be construed as limiting. All percentages are by weight and all solvent mixture proportions are by volume unless otherwise noted.

EXAMPLE 1

Culturing B.t. Isolates

A subculture of the B.t. isolate can be used to inoculate the following peptone, glucose, and salts medium.

| | |
|---|---|
| Bacto Peptone | 7.5 g/l |
| Glucose | 1.0 g/l |
| $KH_2PO_4$ | 3.4 g/l |
| $K_2HPO_4$ | 4.35 g/l |
| Salt Solution | 5.0 ml/l |
| $CaCl_2$ Solution | 5.0 ml/l |
| Salts Solution (100 ml) | |
| $MgSO_4 \cdot 7H_2O$ | 2.46 g |
| $MnSO_4 \cdot H_2O$ | 0.04 g |
| $ZnSO_4 \cdot 7H_2O$ | 0.28 g |
| $FeSO_4 \cdot 7H_2O$ | 0.40 g |
| $CaCl_2$ Solution (100 ml) | |
| $CaCl_2 \cdot 2H_2O$ | 3.66 g |
| pH 7.2 | |

The salts solution and $CaCl_2$ solution are filter-sterilized and added to the autoclaved and cooked broth at the time of inoculation. Flasks are incubated at 30° C. on a rotary shaker at 200 rpm for 64 hr.

The above procedure can be readily scaled up to large fermentors by procedures well known in the art.

The B.t. spores and crystals, obtained in the above fermentation, can be isolated by procedures well known in the art. A frequently-used procedure is to subject the harvested fermentation broth to separation techniques, e.g., centrifugation.

EXAMPLE 2

Production of Activated 201T6 Toxin (201T6-D)

Activated 201T6 toxin can be produced by a variety of methods which result in truncation of the 201T6 toxin. In this regard, reference can be made to WO95/02693. In one such method, cultures of PS201T6 were harvested by centrifugation and resuspended to ⅕th to ¹⁄₂₅th of their original culture volume in 0.1 $Na_2CO_3$/$NaHCO_3$ pH 11.0 containing 0.5 mg/ml pronase E (Sigma Chemical Company, P-5147 Type XIV bacterial protease from Streptomyces griseus). The suspension was incubated at 37° C. overnight with mixing. The suspensions were dialyzed against 2 changes of 50 to 100 volumes each of either distilled water or 0.1 M $Na_2CO_3$/$NaHCO_3$ pH 9.5 to yield "dialyzed suspensions."

The suspension resulting from 0.1 M $Na_2CO_3$/$NaHCO_3$ pH 9.5 dialysis was centrifuged to remove cells, spores, and debris. Additional purification from spores and debris can be accomplished by filtration through a Whatman glass microfibre filter, a 0.8 micron cellulose acetate filter, and a 0.2 micron cellulose acetate filter to yield a "filtered supernatant."

Dried preparations of the processed toxin were prepared either before or after filtration by dialyzing against 2 changes of 50 to 100 volumes distilled water, followed by lyophilization (lyophilized, pronase-treated toxin).

EXAMPLE 3

Alternative Method for Production of Activated 201T6 Toxin

Cultures of PS201T6 were harvested by centrifugation and resuspended to ⅕th to ½₅th of their original culture volume in 0.1 M $Na_2CO_3/NaHCO_3$, 0.5% 2-mercaptoethanol, pH 11.0. The suspension was incubated for about 2 hours at room temperature. The suspension was centrifuged to remove cells, spores, and debris. Additional purification from spores and debris can be accomplished by filtration through a Whatman glass microfibre filter, a 0.8 micron cellulose acetate filter, and a 0.2 micron cellulose acetate filter to yield a "filtered supernatant." The suspensions were dialyzed against 2 changes of 50 to 100 volumes each of either distilled water or 0.1 M $Na_2CO_3/NaHCO_3$ pH 9.5 to yield "dialyzed suspensions." Dried preparations of the processed toxin were prepared either before or after filtration by dialyzing against two changes of 50 to 100 volumes distilled water, followed by lyophilization. Material prepared according to this procedure is referred to herein as 201T6-D.

EXAMPLE 4

Activity of B.t. Isolates Against Second Instar Alfalfa Weevil Hypera postica

The preparations were tested against second instar alfalfa weevil by a top-load bioassay on artificial diet. The agar-based diet was dispensed into individual wells of 96-well, flat-bottom plates, and allowed to solidify before the application of the suspension to the surface of the diet. Trays were gently swirled on a rotary shaker to ensure diet surface coverage with the suspensions. The toxin suspensions on the surface of the diet were allowed to air-dry under a laminar flow hood. A single larva was infested into each well and the plate sealed by a polyester film with heat-sensitive adhesive. The assay trays were held at 23° C., 70% RH, 8:16 day:night cycle for six days. The larvae were observed under a dissection microscope for mortality. Table 3 shows bioassay results from three screens using the artificial diet top-load bioassay in 96-well trays. In Table 3, PS201T6 is the whole lyophilized culture; PS201T6-D is prepared as described in Example 3.

TABLE 3

Bioassay results of B.t. strains against Hypera postica

| Isolate | Screen 1 | | Screen 2 | | Screen 3 | |
|---|---|---|---|---|---|---|
| | µg/cm² | % | µg/cm² | % | µg/cm² | % |
| PS201T6 | 130 | 92 | 85 | 100 | 5 | 100 |
| | 65 | 75 | 32 | 100 | 2.4 | 93 |
| | | | 18 | 100 | 1.2 | 50 |
| | | | 16 | 100 | 0.6 | 18 |
| | | | 8 | 100 | 0.3 | 25 |
| | | | 4 | 100 | | |
| PS201T6-D (activated) | 65 | 100 | 2 | 100 | 2 | 100 |
| | 32 | 100 | 1 | 78 | 1 | 100 |
| | 16 | 100 | 0.5 | 57 | 0.5 | 91 |
| | 8 | 100 | 0.25 | 20 | 0.25 | 73 |
| | 4 | 100 | 0.12 | 0 | 0.12 | 68 |
| MR506 | 65 | 75 | 65 | 70 | 65 | 66 |
| | 32 | 25 | 32 | 46 | 32 | 31 |
| | 16 | 33 | 16 | 25 | 16 | 100 |
| | 8 | 8 | 8 | 37 | 8 | 85 |
| | 4 | 8 | 4 | 13 | 4 | 42 |
| KB92 | 130 | 27 | 130 | 50 | 130 | 87 |
| | 65 | 10 | 65 | 0 | 65 | 75 |
| HD-511 | 130 | 8 | 130 | 0 | 130 | 25 |
| | 65 | 8 | 65 | 14 | 65 | 6 |
| Water | 0 | 0 | 0 | 0 | 0 | 0 |

EXAMPLE 5

Activity of B.t. Isolates Against the Rice Water Weevil

B.t. isolates were evaluated for their insecticidal activity against rice water weevil adults. The insects used in these experiments were collected from rice at the Rice Research Station, Acadia Parish La. The weevils were taken to a laboratory, placed in plastic storage boxes lined with moist paper towels and held at 27° C. with a 16 hour photoperiod. Weevils were provided an excess of rice foliage (var. Cypress) which was replenished every two days. The rice from which weevils were collected was not treated with insecticides during the growing season.

The plants used in the experiments were greenhouse grown Cypress rice. A 16 hour photoperiod was provided by metal halide lamps. The temperature in the greenhouse fluctuated from 27° C. at night to daytime highs in excess of 32° C.

The B.t. formulations were made by adding 10 mg of B.t. isolate to a 2 ml microcentrifuge tube containing 1 ml of a 0.1% aqueous solution of Bond adjuvant. The microcentrifuge tubes were sealed and sonicated for 15 seconds, resulting in the formation of suspensions that were stored at 4° C. until used in the bioassays.

The bioassays were conducted by excising the newest unfurled leaves of greenhouse grown Cypress rice plants and wrapping them in moist paper towels. The excised leaves were taken to the laboratory and gently wiped with a cotton ball saturated with a 0.1% solution of Bond adjuvant before being cut into 2.5–3.5 cm sections. The apical and basal 3 cm of each leaf was discarded. Individual leaf sections were placed into microcentrifuge tubes containing one of the B.t. isolate suspensions. The tubes were sealed and vortexed for 3–5 seconds to uniformly coat the leaf section with the isolate suspension. Leaf sections were placed individually into 5 cm Petri dishes containing two filter paper disks moistened with 8–10 drops of tap water. One adult rice water weevil was added to each dish and the dish was covered and sealed with "PARAFILM" brand film. The Petri dishes were maintained at 27° C. with a 16 hour photoperiod. Every 24 hours the Petri dishes were opened and weevil mortality and extent of feeding were determined.

Percent mortality caused by the isolates is listed below. All treatments, with the exception of the negative controls caused some mortality to the weevils. The MR508 recombinant *E. coli* expresses a toxin obtainable from *B.t.* isolate PS33F2.

TABLE 4

| | | Mortality % | |
|---|---|---|---|
| | Treatment | 2 day | 4 day |
| 1 | Adjuvant | 0 | 10 |
| 2 | PS50C | 20 | 40 |
| 3 | MR506 | 30 | 50 |
| 4 | 201T6-D | 80 | 100 |
| 5 | HD511 | 60 | 80 |
| 7 | KB92 | 20 | 40 |
| 7 | PS86B1 | 30 | 60 |
| 8 | PS201T6 | 30 | 30 |
| 9 | PS101Z2 | 10 | 60 |
| 10 | PS50B | 30 | 60 |
| 11 | MR508 | 30 | 30 |
| 12 | PS204G4 | 20 | 30 |
| 13 | PS204G6 | 30 | 50 |
| 14 | PS167P | 20 | 40 |
| 15 | PS192NL | 20 | 70 |
| 16 | PS201L1 | 30 | 30 |
| 17 | PS169E | 10 | 30 |
| 18 | PS177G | 30 | 40 |
| 19 | PS196S1 | 30 | 30 |
| 20 | PS73E | 40 | 70 |
| 21 | untreated | 0 | 0 |

EXAMPLE 6

Of particular interest according to the subject invention is the use of CryIII *B.t.* toxins and cyt toxins to control weevils. As shown in Table 5, toxins from several subclasses of CryIII toxins, as well as cyt toxins, can be used to effectively control weevils. The CryIII toxins are well known to those skilled in the art. Of particular interest in the subject invention are those toxins which have at least 50% amino acid sequence identity with a toxin selected from the group consisting of CryIIIA, HD511, 50C, or KB92. Preferably, the sequence identity will be more than 75%. The cyt toxins are also well known and are exemplified by, for example, cytA, cytB, and the 201T6 toxin. Again, greater then 50% or 75% sequence identity with these toxins is preferred.

TABLE 5

| Isolate | B.t. toxin | Percent Mortality (4 days) |
|---|---|---|
| PS50C | CryIII | 40 |
| MR525 | CryIIIA | 40 |
| PS86B1 | CryIIIB | 60 |
| HD511 | CryIII | 80 |
| PS50B | CryIII | 60 |
| PS201T6 | cyt (201T6-D) | 100 |
| Untreated | | 0 |

EXAMPLE 7

Activity of *Bacillus thuringiensis* on the Cotton Boll Weevil

Strains of *B.t.* were tested for activity against boll weevil. The *B.t.* strains were provided as powders. Powders were weighed and suspended in distilled water, vortexed, and diluted in distilled water to the desired concentration.

Boll weevil eggs were received on diet from the USDA Boll Weevil Rearing Laboratory, Stoneville, Miss., and maintained in a growth chamber at 30° C., with a 12:12 (L:D) photoperiod, until hatch. *B.t.* strains suspended in 1 ml distilled water were incorporated into 50 ml modified VA+SB diet maintained at 55° C. in 125 ml flasks. The diet/*B.t.* mixture was poured into 15×100 mm plastic petri dishes. A plastic grid was immediately inserted into each diet plate. Twenty-one second instar larvae were placed in each dish. Petri dishes containing diet, *B.t.*, and larvae were covered with parafilm and maintained in a growth chamber as described above. Mortality was evaluated at 24, 48, and 72 hours. Plates were photographed at 72 hours to obtain a qualitative estimate of the amounts of insect burrowing and feeding. Larvae were considered dead at 72 hours if they did not respond to probes with a camel hair brush.

Particularly good activity was observed for *B.t.* isolate PS201T6 and the toxin obtained from this isolate. In a preferred embodiment, the 201T6 protein is processed using procedures such as those which are described in Examples 2 and 3.

Activity against the cotton boll weevil was also observed for *B.t.* strain *bui bui* (KB92).

EXAMPLE 8

Insertion of Toxin Genes Into Plants

One aspect of the subject invention is the transformation of plants with genes coding for a toxin active against weevils. The transformed plants are resistant to attack by weevils.

Genes encoding weevil-active toxins, as disclosed herein, can be inserted into plant cells using a variety of techniques which are well known in the art. Those techniques include transformation with T-DNA using *Agrobacterium tumefaciens* or *Agrobacterium rhizogenes* as transformation agent, fusion, microinjection, bombardment, chemical agent (PEG) assisted DNA uptake, or electroporation as well as other possible methods. If agrobacteria are used for the transformation, the DNA to be inserted has to be cloned into special plasmids, namely either into an intermediate vector or into a binary vector. The intermediate vectors can be integrated into the Ti or Ri plasmid by homologous recombination owing to sequences that are homologous to sequences in the T-DNA. The Ti or Ri plasmid also comprises the vir region necessary for the transfer of the T-DNA. Intermediate vectors cannot replicate themselves in agrobacteria. The intermediate vector can be transferred into *Agrobacterium tumefaciens* by means of a helper plasmid (conjugation).

Binary vectors can replicate themselves both in *E. coli* and in agrobacteria. They comprise a selection marker gene and a linker or polylinker which are framed by the right and left T-DNA border regions. They can be transformed directly into agrobacteria (Holsters et al. [1978] *Mol. Gen. Genet.* 163:181–187). The agrobacterium used as host cell is to comprise a plasmid carrying a vir region. The vir region is necessary for the transfer of the T-DNA into the plant cell.

The use of T-DNA for the transformation of plant cells has been intensively researched and sufficiently described in EP 120 516; Hoekema (1 985) In: *The Binary Plant Vector System*, Offset-durkkerij Kanters B.V., Alblasserdam, Chapter 5; Fraley et al., *Crit. Rev. Plant Sci.* 4:1–46; and An et al. (1985) *EMBO J.* 4:277–287.

Once the inserted DNA has been integrated in the genome, it is relatively stable there and, as a rule, does not come out again. It normally contains a selection marker that confers on the transformed plant cells resistance to a biocide or an antibiotic, such as kanamycin, G 418, bleomycin, hygromycin, or chloramphenicol, inter alia. The individually employed marker should accordingly permit the selection of transformed cells rather than cells that do not contain the inserted DNA.

The bacterium so transformed is used for the transformation of plant cells. Plant explants can advantageously be cultivated with *Agrobacterium tumefaciens* or *Agrobacterium rhizogenes* for the transfer of the DNA into the plant cell. Whole plants can then be regenerated from the infected plant material (for example, pieces of leaf, segments of stalk, roots, but also protoplasts or suspension-cultivated cultivated cells) in a suitable medium, which may contain antibiotics or biocides for selection. The plants so obtained can then be tested for the presence of the inserted DNA. No special demands are made of the plasmids in the case of microinjection and electroporation. It is possible to use ordinary plasmids, such as, for example, pUC derivatives.

The transformed cells grow inside the plants in the usual manner. They can form germ cells and transmit the transformed trait(s) to progeny plants. Such plants can be grown in the normal manner and crossed with plants that have the same transformed hereditary factors or other hereditary factors. The resulting hybrid individuals have the corresponding phenotypic properties.

It should be understood that the examples and embodiments described herein are for illustrative purposes only and that various modifications or changes in light thereof will be suggested to persons skilled in the art and are to be included within the spirit and purview of this application and scope of the appended claims.

The invention claimed is:

1. An isolated, weevil-toxic protein comprising a weevil-toxic fragment of a CryIII-class toxin obtainable from *Bacillus thuringiensis* strain PS50B having accession number NRRL B-21656.

2. The protein of claim 1 wherein said protein is the full-length, CryIII-class toxin obtainable from *Bacillus thuringiensis* strain PS50B having accession number NRRL B-21656.

3. A method of controlling a weevil pest wherein said method comprises contacting said pest with a weevil-toxic amount of a protein wherein said protein comprises a weevil-toxic fragment of a CryIII-class toxin obtainable from *Bacillus thuringiensis* strain PS50B having accession number NRRL B-21656.

4. The method according to claim 3 wherein said protein is the full-length, CryIII-class toxin obtainable from *Bacillus thuringiensis* strain PS50B having accession number NRRL B-21656.

5. The method according to claim 3 wherein said weevil is a rice water weevil.

6. A method of controlling rice water weevils wherein said method comprises administering to said weevils a pesticidally effective amount of a toxin obtainable from *Bacillus thuringiensis* isolate PS33F2, or a weevil-toxic fragment of said toxin.

7. The method according to claim 3 wherein said toxin, or said fragment thereof, is produced by a plant.

8. The method according to claim 6 wherein said toxin, or said fragment thereof, is produced by a plant.

* * * * *

UNITED STATES PATENT AND TRADEMARK OFFICE
CERTIFICATE OF CORRECTION

PATENT NO.        : 7,091,177 B2  
APPLICATION NO.   : 10/631405  
DATED             : August 15, 2006  
INVENTOR(S)       : Gregory Alan Bradfisch, H. Ernest Schnepf and Leo Kim It is certified that error appears in the above-identified patent and that said Letters Patent is hereby corrected as shown below:

Column 4,

Line 10, "hosts maybe," should read --hosts may be,--

Column 14,

Line 61, "Hoekema (1 985)" should read --Hoekema (1985)--

Signed and Sealed this

Fourth Day of December, 2007

JON W. DUDAS  
*Director of the United States Patent and Trademark Office*